US006790944B1

(12) United States Patent
Ishiwata et al.

(10) Patent No.: US 6,790,944 B1
(45) Date of Patent: Sep. 14, 2004

(54) DNA ENCODING IGA NEPHROPATHY INDICATING PROTEIN

(75) Inventors: Tetsuyoshi Ishiwata, Machida (JP); Mikiko Sakurada, Machida (JP); Ayako Kawabata, Sagamihara (JP); Satoshi Nakagawa, Machida (JP); Tetsuro Kuga, Hofu (JP); Tatsunari Nishi, Higashimina (JP); Nobuo Nomura, Kisarazu (JP); Takahiro Nagase, Kisarazu (JP); Shigemasa Sawada, Mushashino (JP); Masami Takei, Sayama (JP)

(73) Assignees: Kyowa Hakko Kogyo Co., Ltd., Tokyo (JP); Kazusa DNA Research Institute Foundation, Chiba (JP)

( * ) Notice: Subject to any disclaimer, the term of this patent is extended or adjusted under 35 U.S.C. 154(b) by 0 days.

(21) Appl. No.: 09/129,603

(22) Filed: Aug. 5, 1998

Related U.S. Application Data

(63) Continuation-in-part of application No. PCT/JP97/04469, filed on Dec. 5, 1997.

(30) Foreign Application Priority Data

Dec. 5, 1996 (JP) .............................................. 8-325752

(51) Int. Cl.⁷ ........................ C07H 21/02; C12N 15/85; C12P 19/34; C12Q 1/68
(52) U.S. Cl. .......................... 536/23.1; 435/6; 435/325; 435/91.2
(58) Field of Search .......................... 435/6, 91.2, 325, 435/326.1, 320.1; 536/23.1, 24.5, 23.5, 24.3; 424/93.1, 93.2, 93.21; 530/350

(56) References Cited

U.S. PATENT DOCUMENTS 5,225,326 A * 7/1993 Bresser et al. .................. 435/6

FOREIGN PATENT DOCUMENTS

JP WO-95/14772 * 6/1995

OTHER PUBLICATIONS

Hiller, L. et al., Genbank Accession No. N21024, Dec. 1995, Unpublished (1995).*
Hiller et al., Generation and Analysis of 280,000 Human Expressed Sequence Tags, 1996, Genome Research, vol. 6, pp. 807–828.*
Nagase et al. Accession No. o00234, D87078, Jul. 1997.*
Branch AD. TIBS 23, p. 45–50, Feb. 1998.*
Crooke ST, ed. Antisense Research and Application. Springer Press, p. 1–49, 1998.*
Kendrew J, ed. The Encyclopedia of Molecular Biology. Blackwell Science Inc. p. 503–505, 1994.*
Plenat F. Molecular Medicine Today. p. 250–257, Jun. 1996.*
Agrawal S. Tibtech. 14: 376–387, Oct. 1996.*
Biolabs Catalog 1988–1989, #1230, 1989.*
O'Hara, et al., "Homo sapiens mRNA for KIAA0099 Protein, partial cds." (1997) Accession No. XP–002208794.
O'Hara, et al., "Homo sapiens mRNA for KIAA0235 protein, partial cds" (1994) Accession No. XP–002208795.
"Perspectives in Clinical Nephrology IGA Nephropathy", *Kidney International*, vol. 47, No. 2 (1995), pp. 377–387 (XP–002940424).
Namie, et al., "Expression and Function of Fibronectin Receptors on Peripheral Mononuclear cells in IGA Nephropathy", *Nephrology Dialysis Transplantation* vol. 10 (1995), pp. 1342–1347.
Nagase, et al., "Hypothetical protein KIAA0099 (Pumilio 1) (Fragment)", 1996, Accession No. Q14671 XP–002208796.
DNA Research, vol.3 (Oct. 1996), pp. 321–329.

* cited by examiner

*Primary Examiner*—Karen A. Lacourciere
(74) *Attorney, Agent, or Firm*—Fitzpatrick, Cella, Harper & Scinto

(57) ABSTRACT

The present invention relates to a novel protein isolated from the leukocyte of IgA nephropathy patients, and DNA encoding the protein. It also relates to an oligonucleotide based on the nucleotide sequence complementary with the DNA, an antibody which specifically reacts with the protein and, furthermore, diagnostic and therapeutic drugs of IgA nephropathy comprising it.

5 Claims, 1 Drawing Sheet

DNA ENCODING IGA NEPHROPATHY INDICATING PROTEIN

CROSS-REFERENCE TO RELATED APPLICATION

This is a continuation-in-part application of PCT/JP97/04469 filed on Dec. 5, 1997.

BACKGROUND OF THE INVENTION

1. Field of the Invention

The present invention relates to a novel protein whose expression level fluctuates in leukocytes of IgA nephropathy patients in comparison with leukocytes of healthy persons, an antibody against the protein, DNA encoding the protein, methods for detecting the protein using the antibody, mRNA and DNA using a primer comprising a complementary nucleotide sequence to the DNA, and diagnosis and treatment of IgA nephropathy.

2. Brief Description of the Background Art

IgA nephropathy is a chronic glomerulonephritis which is characterized in that an IgA immune complex considered to be originated from blood deposits in glomerulus of the kidney. In Japan, the IgA nephropathy occupies 30% or more of primary renal diseases, and is the most common renal disease. Moreover, 15 to 30% of the patients with IgA nephropathy achieve renal failure due to poor prognosis. However, since the underlying cause of IgA nephropathy is still unclear, a fundamental therapeutic method has not been found. Additionally, definite diagnosis of IgA nephropathy imposes heavy burden on patients, because the method is carried out by removing a portion of the kidney by biopsy and recognizing deposition of the IgA immune complex in mesangium by means of an immunological staining.

It has been reported that about 50% of the patients with IgA nephropathy have a high blood IgA level [*Diseases of the Kidney*, 5th edition (1993), *Nephron*, 29, 170 (1981)]. It is considered that B cells relate to the production of IgA in blood and T cells relate to the regulation of the production. Furthermore, it has been reported that the production of cytokine, such as interleukin 4, interleukin 5, interleukin 6 or TGF-β (transforming growth factor-β), is high in peripheral T cells of IgA nephropathy patients in comparison with healthy persons [*Clinical & Experimental Immunology*, 103, 125 (1996), *Kidney International*, 46, 862 (1994))] and that integrin, such as VLA (very late activation)-4 and VLA-5, are strongly activated in peripheral lymphocytes of IgA nephropathy patients [*Nephrology, Dialysis, Transplantation*, 10, 1342 (1995)].

On the basis of these facts, it is considered that, in IgA nephropathy, excessive IgA is produced due to abnormality in the immune system, the resulting IgA immune complex in blood deposits on the glomerulus, and the complement system is activated on the deposited IgA immune complex and the like to exert influence and cause disorders of the glomerulus. However, the cause of IgA nephropathy has not yet been determined.

SUMMARY OF THE INVENTION

Elucidation of the cause of IgA nephropathy, as well as a treatment or diagnosis which can reduce a burden on patients are long-sought. The present invention provides a novel protein which has been determined to have increased expression level in leukocytes of IgA nephropathy patients, as well as an antibody against the protein, DNA encoding the protein, methods for detecting the protein using the antibody, mRNA and DNA using the oligonucleotide comprising a complementary nucleotide sequence to the DNA, and diagnostic and therapeutic agents of IgA nephropathy.

The present invention relates to a protein comprising the amino acid sequence represented by SEQ ID NO:2; DNA encoding the protein of the present invention; DNA which comprises the nucleotide sequence represented by SEQ ID NO:1; and DNA which hybridizes with the DNA comprising the above nucleotide sequence under stringent conditions. Furthermore, the present invention relates to a recombinant vector which comprises the DNA and a vector; a transformant obtained by introducing the recombinant vector into a host cell; and a process for producing the protein, comprising culturing the transformant in a medium to produce and accumulate the protein of the present invention in the culture, and recovering the protein from the resulting culture.

Moreover, the present invention relates to a method for detecting the mRNA derived from the protein of the present invention using an oligonucleotide comprising a portion of the nucleotide sequence of the DNA of the present invention or a portion of the nucleotide sequence complementary to the DNA, for example, the oligonucleotide represented by SEQ ID NO:6 or NO:7; and IgA nephropathy diagnostic agents comprising the oligonucleotide.

Also, the present invention relates to a method for inhibiting expression of the protein of the present invention using an oligonucleotide comprising a portion of the nucleotide sequence of the DNA of the present invention or a portion of the nucleotide sequence complementary to the DNA, for example, the oligonucleotide represented by SEQ ID NO:6 or NO:7; and IgA nephropathy therapeutic agents comprising the oligonucleotide.

Additionally, the present invention relates to an antibody which specifically reacts with the protein of the present invention; a method for immunologically detecting the protein of the present invention using the antibody of the present invention; and IgA nephropathy diagnostic and therapeutic agents comprising the antibody.

DETAILED DESCRIPTION OF THE INVENTION

Figure 1:
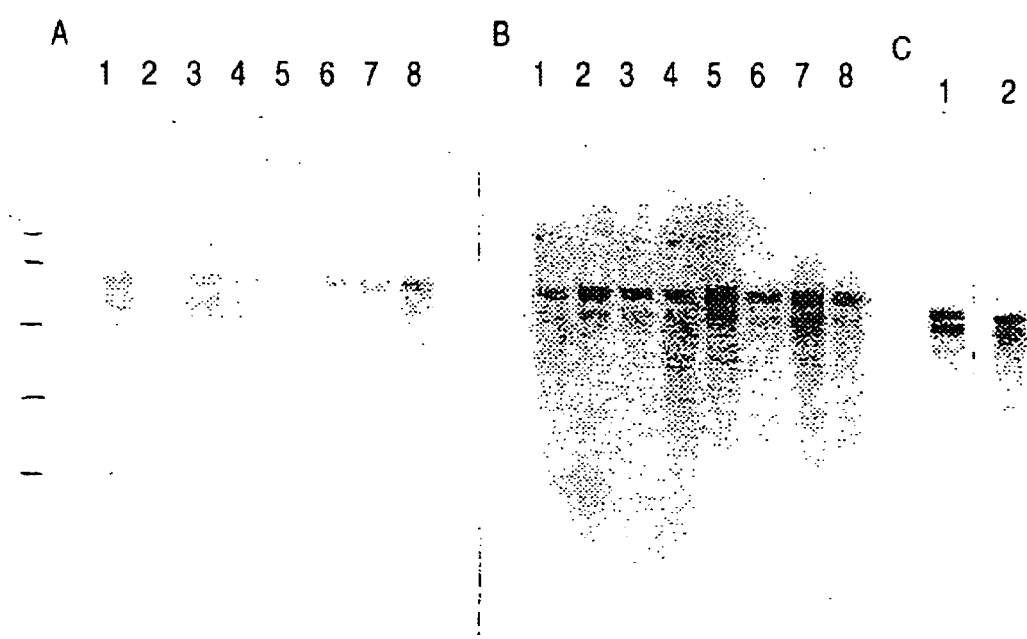
FIG. 1 shows an autoradiograph of the Northern blot of KIAA0235 in human tissue and cell in Example 5. Both A and B are results of human tissue, wherein A represents the autoradiograph of the filter blotting each RNA of 1: pancreas, 2: kidney, 3: skeletal muscle, 4: Liver, 5: lung, 6: placenta, 7: brain, and 8: heart, and B represents the autoradiograph of the filter blotting each RNA of 1: peripheral leukocyte, 2: colon, 3: small intestine, 4: ovary, 5: testis, 6: prostate, 7: thymus, and 8: spleen. C is a result of human cell line, which represents the autoradiograph of the filter blotting the RNA of 1: HeLa and 2: KG-1. Lines at the leftmost end of A correspond to the RNA marker positions indicating 9.5 kb, 7.5 kb, 4.4 kb, 2.4 kb and 1.35 kb from the top.

This application is based on Japanese application No. 8-325752 filed on Dec. 5, 1996 and PCT/JP97/04469 filed on Dec. 5, 1997, the entire contents of which are incorporated hereinto by reference.

The protein of the present invention includes, for example, a protein comprising the amino acid sequence represented by SEQ ID NO:2. The DNA of the present invention includes a DNA sequence encoding the protein of the present invention, a DNA sequence comprising the nucleotide sequence represented by SEQ ID NO:1, a DNA sequence which hybridizes with the DNA under stringent conditions, and the like.

The DNA encoding the protein of the present invention includes DNAs having a nucleotide sequence different from the nucleotide sequence represented by SEQ ID NO:1 because generally there are various genetic codes per one amino acid. Those of ordinary skill in this art are well-aware of how to substitute one or more degenerate codons to create an equivalent DNA encoding the same protein sequence. This includes, for example, selecting degenerate codons which may be more common in a particular expression system, such as yeast.

Furthermore, the DNA which hybridizes under stringent conditions with a DNA comprising a nucleotide sequence represented by SEQ ID NO:1 means a DNA in which a mutation, such as substitution, deletion, insertion, addition and the like, is introduced at least one portion within the range that the inherent activities of the protein are not lost, and a DNA which is obtained by colony hybridization or plaque hybridization [*Molecular Cloning, A Laboratory Manual*, Second Edition (edited by Sambrook, Fritsch and Maniatis, Cold Spring Harbor Laboratory Press (1989)) (referred to as "*Molecular Cloning, A Laboratory Manual*, 2nd ed." hereinafter) using, as a probe, a DNA comprising a nucleotide sequence represented by SEQ ID NO:1 or a fragment thereof.

The preparation and expression of the DNA encoding the novel protein of the present invention is carried out according to the process described in *Molecular Cloning, A Laboratory Manual*, 2nd ed., *Current Protocols in Molecular Biology, Supplement 1 to 34* (edited by Ausubel, Brent, Kingston, Moore, Seidman, Smith and Struhl, published by Green Publishing Associates and Wiley-Interscience, 1987–1996 edition) (referred to as "*Current Protocols in Molecular Biology, Supplement 1 to 34*"), and the like.

In the present invention, in order to obtain a novel protein, taking note of the difference in the expression quantity of mRNA in leukocytes between patients with IgA nephropathy and healthy persons, the differential display method [*FEBS Letters*, 351, 231 (1994)] is used. The differential display method is a method in which cloning of a novel gene is carried out using pattern of expression as an index. That is, an amplified cDNA fragment of a novel gene whose expression level increases or decreases significantly in leukocytes of a patient with IgA nephropathy as compared with leukocytes of a healthy person is obtained by subjecting total RNA or mRNA extracted from cells to the polymerase chain reaction (PCR) using various primers. At the same time, a cDNA library is constructed from human undifferentiated myeloid cell line KG-1, and all nucleotide sequences of cDNA of respective clone are determined to form a database beforehand. The homology between the nucleotide sequence of the clone therein and the above-described amplified cDNA fragment is identified, and a novel full-length cDNA is obtained. This method is described below.

Examples of the method for the preparation of a total RNA from leukocytes of patients with IgA nephropathy and leukocytes of healthy persons include guanidine thiocyanate-cesium trifluoroacetate method [*Methods in Enzymol.*, 154, 3 (1987)], the AGPC method (*Jikken Igaku*, 9, 1937 (1991)), RNeasy kit for recovering RNA (produced by QIAGEN), and the like.

Examples of the method for preparing poly(A)$^+$ RNA from the total RNA include oligo(dT)-immobilized cellulose column method (*Molecular Cloning, A Laboratory Manual*, 2nd ed.) and the like. Also, examples of the kit for preparing mRNA from leukocytes of patients with IgA nephropathy and leukocytes of healthy persons include Fast Track mRNA Isolation Kit (manufactured by Invitrogen), Quick Prep mRNA Purification Kit (manufactured by Pharmacia), and the like.

Using an anchor primer, cDNA is synthesized in the usual way from the RNA extracted by the above-described method from leukocytes of a patient with IgA nephropathy or leukocytes of a healthy person, and PCR is carried out using an anchor primer having a 5'-end labeled with fluorescence and an arbitrary primer. The anchor primer is a primer in which an oligonucleotide of adenine, guanine or cytosine, excluding thymidine, is added to the 3'-end of an oligo(dT) sequence which hybridizes with a 3'-end poly(A) sequence of mRNA. The arbitrary primer is typically an oligonucleotide which amplifies various cDNA sequences and can yield a large number of amplified cDNA fragments by a single reaction. Preferably, the oligonucleotide has a length of about 10 mer.

After the PCR, each of the amplified cDNA is subjected to polyacrylamide gel electrophoresis, and the electrophoresis pattern of the amplified cDNA fragment is compared by detecting the fluorescence with a fluorimager. The cDNA fragment which can be amplified by only leukocytes of a patient with IgA nephropathy is extracted from the gel, the amplified cDNA fragment is inserted into a vector, and the nucleotide sequence of the DNA is determined by a usually used nucleotide sequence analyzing method such as the dideoxy method of Sanger et al. [*Proc. Natl. Acad. Sci. USA*, 74, 5463 (1977)], or like.

Examples of the vector to which the DNA fragment is inserted include pDIRECT [*Nucleic Acids Research*, 18, 6069 (1990)], pPCR-Script Amp SK(+) [manufactured by Stratagene, *Strategies*, 5, 6264 (1992)], pT7Blue (manufactured by Novagen), pCR II [manufactured by Invitrogen, *Biotechnology*, 9, 657 (1991)], pCR-TRAP (manufactured by Genehunter), pNoTA$_{T7}$ (manufactured by 5'→3') and the like.

The analysis of the nucleotide sequence is carried out by using a nucleotide sequence automatic analyzer, such as 373A•DNA (manufactured by Applied Biosystems), and the like.

Full-length cDNA can be obtained by carrying out screening according to hybridization using the above-described amplified cDNA fragment as the probe and various cDNA libraries. Also, as in the present invention a clone having the full-length cDNA can be obtained by constructing a cDNA library in advance, determining all nucleotide sequences of a respective clone to form a data base, and then screening a clone having the nucleotide sequence of the above-described amplified cDNA fragment. The method for preparing a cDNA library will be described.

Examples of the method for the preparation of the cDNA library include methods described in *Molecular Cloning, A Laboratory Manual*, 2nd. ed., or *Current Protocols in Molecular Biology, Supplement 1 to 34*, methods using a commercially available kit, such as Super Script™ Plasmid System for cDNA Synthesis and Plasmid Cloning (manufactured by Life Technologies) or ZAP-cDNA Synthesis Kit (manufactured by Stratagene), and the like.

In the preparation of the cDNA library, the vector to which the cDNA, synthesized using mRNA extracted from human undifferentiated myeloid IgA line KG-1 as a template, is inserted may be any vector so long as the cDNA can be inserted thereto. Examples include ZAP Express [*Strategies*, 5, 58 (1992)], pBluescript II SK(+) [*Nucleic Acids Research*, 17, 9494 (1989)], λ zap II (manufactured by Stratagene), λgt10, λgt11 [*DNA Cloning, A Practical Approach*, 1, 49, (1985)], Lambda BlueMid (manufactured by Clonetech), λExCell, pT7T318U (manufactured by Pharmacia), pcD2 [*Mol. Cell. Biol.*, 3, 280 (1983)], pUC18 [*Gene*, 33, 103 (1985)], and the like.

With regard to the *Escherichia coli* for introducing the cDNA library constituted by the vector, any microorganism belonging to *Escherichia coli* can be used so long as the introduction, expression and maintenance of the cDNA library can be conducted. Examples include *Escherichia coli* KL1-Blue MRF' [*Strategies*, 5, 81, (1992)], *Escherichia coli* C600 *Genetics*, 39, 440 (1954)], *Escherichia coli* Y1088, *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1996)], *Escherichia coli* JM105 [*Gene*, 38, 275 (1985)], and the like.

The cDNA can be also obtained without preparing a cDNA library by the 5'-RACE (rapid amplification of cDNA ends) and 3'-RACE [*Proc. Natl. Acad. Sci. USA*, 85, 8998 (1988)] in which adapters are added to both ends of the cDNA and then PCR is carried out using primers based on the nucleotide sequence of the adapter and the nucleotide sequence of the amplified fragment. Alternatively, the cDNA can be obtained by PCR based on the nucleotide sequence represented by SEQ ID NO:1 or a chemical synthesis method using a DNA synthesizer.

A cDNA clone can be selected from the cDNA library according to a colony hybridization or plaque hybridization method (*Molecular Cloning, A Laboratory Manual*, 2nd ed.) using a probe labeled with an isotope or fluorescence. The cDNA may be also prepared according to the polymerase chain reaction (PCR) [*Molecular Cloning, A Laboratory Manual*, 2nd ed. or *Current Protocols in Molecular Biology*, Supplement 1 *to* 34] by preparing a primer and using, as a template, cDNA synthesized from poly (A)$^+$RNA or mRNA, or cDNA library.

The nucleotide sequence of the DNA can be determined by cleaving the cDNA clone selected by the above method with an appropriate restriction enzyme, cloning to a plasmid, such as pBluescript KS(+) (manufactured by Stratagene) or the like, and then analyzing by a conventional nucleotide sequence analysis method, such as dideoxy method of Sanger et al. [*Proc. Natl. Acad. Sci., U.S.A.*, 74, 5463 (1977)] or the like. The nucleotide sequence can be analyzed by using a nucleotide sequence automatic analyzer, such as 373A•DNA sequencer (manufactured by Applied Biosystems) or the like.

A transformant which expresses the protein of the present invention can be obtained by preparing a transformed vector to which the full-length DNA prepared according to the above method is inserted into a downstream site of the promoter in an appropriate vector.

As the host cell, any bacterium, yeast, animal cell, insect cell, and the like, can be used so long as they can express the gene of interest. Examples of the bacterium include bacteria belonging to the genus Escherichia, Serratia, Corynebacterium, Brevibacterium, Pseudomonas, Bacillus, Microbacterium and the like, for example *Escherichia coli, Bacillus subtilis, Bacillus amyloliquefaciens, Brevibacterium flavum, Brevibacterium lactofermentum, Corynebacterium glutamicum, Microbacterium ammoniaphilum,* and the like. Examples of the yeast include *Saccharomyces cerevisiae, Schizosaccharomyces pombe, Kluyveromyces lactis, Trichosporon pullulans, Schwanniomyces alluvius* and the like. Examples of the animal cell include human Namalwa cell, monkey COS cell, Chinese hamster CHO cell, and the like. Examples of the insect cell include *Spodoptera frugiperda* oocytes Sf9 and Sf21 (*Bacurovirus Expression Vectors, A Laboratory Manual*, Oreilly, Miller and Luckow, W.H. Freeman and Company, New York (1992) (referred to as "*Bacurovirus Expression Vectors, A Laboratory Manual*" hereinafter)), *Trichoplusia ni* oocyte Tn5 (High 5, manufactured by Pharmigen), and the like.

Any vector can be used as the vector to which the DNA of the present invention is inserted so long as it can introduce the DNA and drive the expression in the host cell.

When a bacterium, such as *Escherichia coli*, is used as the host cell, it is preferred that the vector is constituted by a promoter, a ribosome binding sequence, the DNA of the present invention and a transcription termination sequence. A promoter controlling gene may be also contained.

Examples of the expression vector include pKYP10 (Japanese Published Unexamined Patent Application No. 110600/83), pLSA1 [*Agric. Biol. Chem.*, 53, 277 (1989)], pGEL1 [*Proc. Natl. Acad. Sci. USA*, 82, 4306 (1985)], and the like.

With regard to the promoter, any promoter can be used so long as it can drive the expression in the host cell. Examples include promoters originated from *Escherichia coli*, phage and the like (for example, trp promoter (Ptrp), lac promoter (Plac), T7 lac promoter, PL promoter, PR promoter, and the like). Also, artifically designed and modified promoters, such as a promoter in which two Ptrp are linked in series (Ptrp×2), tac promoter, and the like, can be used.

With regard to the ribosome binding sequence, it is preferred to use a plasmid in which the space between Shine-Dalgarno sequence (referred to as "SD sequence" hereinafter) and the initiation codon is adjusted to an appropriate distance (for example, 6 to 18 bases).

With regard to the recombinant rector of the present invention, it is preferred to substitute a suitable nucleotide in order that the nucleotide sequence of the DNA of the present invention forms a codon suitable for the expression of a host cell.

The transcription termination sequence is not always necessary for the recombinant vector of the present invention. However, it is preferred to arrange the transcription terminating sequence just downstream of the structural gene.

With regard to the method for the introduction of the recombinant vector to the bacterium, any one of the known methods for introducing DNA into the bacterium, such as a method in which calcium ion is used [*Proc. Natl. Acad. Sci. USA*, 69, 2110 (1972)], a protoplast method (Japanese Published Unexamined Patent Application No. 2483942/88), and the like, can be used.

When yeast is used as the host cell, YEp13 (ATCC 37115), YEp24 (ATCC 37051), YCp50 (ATCC 37419), or the like is used as the expression vector. Any promoter can be used so long as it can drive the expression in yeast. Examples include promoters of genes in the glycolysis system (for example, hexosekinase, and the like), gal 1 promoter, gal 10 promoter, heat shock protein promoter, MFα1 promoter, CUP 1 promoter and the like.

With regard to the method for the introduction of the recombinant vector, any one of known methods for introducing DNA into yeast, such as an electroporation method [*Methods. Enzymol.*, 194, 182–187 (1990)], a spheroplast method [*Proc. Natl. Acad. Sci. USA*, 84, 1929–1933 (1978)], a lithium acetate method [*J. Bacteriol.*, 153, 163–168 (1983)], and the like can be used.

When animal cells are used as the host cells, pAGE107 [Japanese Published Unexamined Patent Application No. 22979/91; *Cytotechnology*, 3, 133 (1990)], pAS3-3 (Japanese Published Unexamined Patent Application No. 227075/90), pAMoERC3Sc, pcDM8 [*Nature*, 329, 840 (1987)], pcDNAI/Amp, pcDNAI (both manufactured by Funakoshi), and the like can be exemplified as the expression vector. Any promoter can be used so long as it can drive the expression in animal cell. Examples include a promoter of IE (immediate early) gene of cytomegalovirus (CMV), a promoter of SV40 or metallothionein, and the like. Also, the enhancer of the IE gene of human CMV may be used together with the promoter.

With regard to the method for the introduction of the recombinant vector into animal cells, any one of the known methods for introducing DNA into animal cells, such as an electroporation method [*Cytotechnology*, 3, 133 (1990)], a calcium phosphate method (Japanese Published Unexamined Patent Application No. 227075/90), a lipofection method [*Proc. Natl. Acad. Sci. USA*, 84, 7413 (1987)], and the like can be used.

When an insect cell is used as the host cell, the protein can be expressed by known methods described in, for example, *Current Protocols in Molecular Biology*, supplement 1–34; Bacurovirus Expression Vectors, A Laboratory Manual;or the like. That is, a recombinant gene transfer vector and bacurovirus are simultaneously introduced into an insect cell to obtain a recombinant virus in an insect cell culture supernatant, and then insect cells are infected with the thus obtained recombinant virus to obtain protein expression insect cell.

Examples of the gene transfer vector include pVL1392, pVL1393, pBlueBacIII (all manufactured by Invitrogen), and the like.

Examples of the bacurovirus include Autographa californica nuclear polyhedrosis virus with which insects of the family Barathra are infected, and the like.

The method for the co-transfer of the above-described recombinant gene transfer vector and the above-described bacurovirus for the preparation of the recombinant virus include a calcium phosphate method (Japanese Published Unexamined Patent Application No. 227075/90), a lipofection method [*Proc. Natl. Acad. Sci. USA*, 84, 7413 (1987)], and the like.

With regard to the gene expression method, a secreted protein production, a fusion protein expression and the like can be effected in accordance with the method described in J. Sambrook et al. (*Molecular Cloning*, 2nd, ed.) in addition to the direction expression.

When expressed in a yeast, an animal cell or a insect cell, a protein to which sugar or sugar chain is added by exo- and endo-glycosidase can be obtained.

The protein of the present invention can be produced by culturing the thus obtained transformant in a culture medium to produce and accumulate the protein of the present invention, and recovering the protein from the resulting culture. Culturing of the transformant of the present invention in a culture medium is carried out in accordance with a usual method used in culturing of host cells.

The medium for culturing the transformant obtained by using as the host cell a microorganism, such as *Escherichia coli*, yeast or the like, may be either a natural medium or a synthetic medium, so long as it contains a suitable carbon source, a suitable nitrogen source, and a suitable inorganic salt and the like, which enables culturing the transformant efficiently.

Examples of the carbon source include carbohydrates (for example, glucose, fructose, sucrose, molasses, starch, starch hydrolysate, and the like), organic acids (for example, acetic acid, propionic acid, and the like), and alcohols (for example ethanol, propanol, and the like).

Examples of the nitrogen source include ammonia, various ammonium salts of inorganic acids or organic acids (for example, ammonium chloride, ammonium sulfate, ammonium acetate, ammonium phosphate, and the like), other nitrogen-containing compounds, peptone, meat extract, yeast extract, corn steep liquor, casein hydrolysate, soybean meal and soybean meal hydrolysate, various fermented cells and hydrolysates thereof, and the like.

Examples of inorganic substance include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out under aerobic conditions by means of shaking, aeration stirring or the like at 15 to 45° C. for 16 to 96 hours. The pH of the medium is maintained at 3.0 to 9.0 during the culturing. Adjustment of the medium pH is carried out using an inorganic or organic acid, an alkali solution, urea, calcium carbonate, ammonia and the like.

Also, antibiotics (for example, ampicillin, tetracycline, and the like) may be added to the medium during the culturing as occasion demands.

When a microorganism transformed with an expression vector containing an inducible promoter is cultured, an inducer may be added to the medium as occasion demands. For example, isopropyl-β-D-thiogalactopyranoside (IPTG) or the like may be added to the medium when a microorganism transformed with an expression vector containing lac promoter is cultured, or indoleacrylic acid (IAA) or the like may by added thereto when a microorganism transformed with an expression vector containing trp promoter is cultured.

Examples of the medium used in the culturing of a transformant obtained using an animal cell as the host cell include RPMI 1640 medium, Eagle's MEM medium, and any one of these media further supplemented with fetal calf serum. The culturing is carried out generally at a temperature of 35 to 37° C. for a period of 3 to 7 days in the presence of 5% $CO_2$. As occasion demands, antibiotics (for example, kanamycin, penicillin, and the like) may be added to the medium during the culturing.

Examples of the medium used in the culturing of a transformant obtained using an insect cell as the host cell include TNM-FH medium (manufactured by Pharmingen), Sf900 II SFM (manufactured by Life Technologies), ExCell 400 or ExCell 405 (both manufactured by JRH Biosciences), and the like. The culturing is carried out generally at a temperature of 25 to 30° C. for a period of 1 to 4 days. Additionally, antibiotics (for example, gentamicin, and the like) may be added to the medium during the culturing as occasion demands.

When the protein of the present invention is expressed in a dissolved state inside the cells, the cells after completion of the culturing are recovered by centrifugation, suspended in an aqueous buffer and then disrupted by ultrasonic, French press or the like to obtain the protein from a supernatant fluid prepared by centrifugation. Also, when the protein forms an inclusion body, the inclusion body is solubilized using a protein denaturing agent, and then the solubilized solution is diluted to or dialyzed against a solution containing no protein denaturing agent or a dilute solution containing a protein denaturing agent in such a concentration that the protein is not denatured in order to form a renatured protein.

When the protein of the present invention or a derivative thereof, such as a sugar-modified product or the like, is secreted outside the cells, the protein or the derivative, such as a sugar-modified product or the like, can be recovered from the culture supernatant. That is, the isolation and purification can be conducted by using isolation steps, such as solvent extraction, fractional precipitation by an organic solvent, salting-out, dialysis, centrifugation, ultrafiltration, ion exchange chromatography, gel filtration chromatography, hydrophobic interaction chromatography, affinity chromatography, reverse, phase chromatography, crystallization, electrophoresis, and the like, alone or as a combination thereof.

Furthermore, the protein of the present invention can be prepared according to a chemical synthesis method based on the amino acid sequence represented by SEQ ID NO:2.

Examples of a method for detecting the mRNA of a novel protein using the oligonucleotide based on the nucleotide sequence of the DNA of the present invention includes Northern hybridization [*Molecular Cloning, A Laboratory Manual*, 2nd ed., Cold Spring Harbor Laboratory Press (1989)], PCR [*PCR Protocols*, Academic Press (1990)], and the like. Particularly, RT (Reverse Transcribed)-PCR is simple and easy and can therefore be applied to the diagnosis of IgA nephropathy. Specifically, the amplified fragment is detected by collecting blood from human to recover leukocyte, transforming the RNA isolated therefrom into cDNA using an oilgo(dT) primer and a reverse transcriptase into, and conducting PCR using a pair of oligonucleotide primers corresponding to the mRNA to be detected.

Examples of the oligonucleotide primers include a sense primer corresponding to the 5'-end side nucleotide sequence, and an antisense primer corresponding to the 3'-end side nucleotide sequence, of a portion of the mRNA to be detected. In this case, the nucleic acid corresponding to uracil in mRNA corresponds to thymidine in the oligonucleotide primer.

As the sense primer and antisense primer, it is preferred to use oligonucleotides in which melting point ($T_s$) and the number of bases are not significantly different from each other. Preferably, the base number is 15 to 40 mer.

The nucleotide sequence moiety to be amplified using the above oligonucleotide primer may be any nucleotide sequence region of the mRNA, but a nucleotide sequence region which has a length of 50 bp to 2 kbp and does not contain a sequence rich in a repeating sequence or GC (guanine-cytosine) bases is preferred.

Furthermore, the expression of the protein can be inhibited by repressing the transcription of DNA or translation of mRNA using an antisense RNA/DNA [*Chemistry*, 46, 681 (1991), *Biotechnology*, 9, 358 (1992)]. The inhibition of production of the protein using anti-sense RNA/DNA technology can be carried out by designing and preparing an oligonucleotide based on the nucleotide sequence of a portion of the DNA encoding the protein of the present invention, preferably that of 10 to 50 bases positioned in the translation initiation site, and administrating it in vivo. As the nucleotide sequence of the synthetic oligonucleotide, those which partially comprises the nucleotide sequence of the antisense chain of the DNA encoding of the protein of the present invention, or those which have been modified to the extent not to lose the activity of inhibiting the expression of the protein activity can be used. As oligonucleotide, DNA, RNA or their derivatives, such as methyl or phosphorothioate derivatives, can be used.

The antibody can be produced by immunizing an animal using the protein of the present invention as an antigen or a peptide, chemically synthesized based on the amino acid sequence represented by SEQ ID NO:2 which is a protein of the present invention. A monoclonal antibody to the protein of the present invention can be prepared by preparing a hybridoma through fusion of the antibody producing cells with myeloma cells of an animal and culturing the hybridoma, or administering the hybridoma to the animal to induce ascites tumor in the animal, and then isolating and purifying it from the culture medium or ascitic fluid. Also, a polyclonal antibody to the protein of the present invention can be prepared by isolating the immune serum of the immune animal.

Using the antibody of the present invention, the IgA nephropathy-related protein can be detected or determined immunologically.

Examples of the immunological detection method include ELISA method using a microtiter plate, fluorescent antibody technique, western blot technique, immunohistochemical staining and the like.

Examples of the immunological determination method include sandwich ELISA method in which, among antibodies which react with the protein of the present invention in solution, two monoclonal antibodies having different epitopes are used and radioimmunoassay method in which the protein of the present invention labeled with radioactive isotope, such as $^{125}I$ or the like, and an antibody which recognizes the protein of the present invention are used.

Using the antibody of the present invention, the presence or absence of IgA nephropathy in a person to be inspected can be diagnosed by immunologically detecting or determining an IgA nephropathy-related protein in leukocytes collected from a healthy person and the person to be inspected, comparing its amounts in the healthy person and person to be inspected and then examining the quantitative fluctuation. As a specific sample to be tested, leukocytes separated from peripheral blood samples of a healthy person and a person to be inspected can be used. Additionally, when the IgA nephropathy-related protein to be detected is a protein secreted from leukocytes, the presence or absence of IgA nephropathy in a person to be inspected can be detected and diagnosed by immunologically detecting or determining the protein in blood plasma samples collected from a healthy person and the person to be inspected, comparing its amounts in the healthy person and person to be inspected and then examining its quantitative fluctuation.

The antibody of the present invention can be applied to the treatment or prevention of IgA nephropathy.

When the DNA, protein, oligonucleotide and antibody is used for the diagnosis, treatment or prevention of IgA nephropathy, a diagnostically or pharmacologically acceptable carrier may be added.

EXAMPLES

Examples of the present invention are given below by way of illustration and not by way of limitation.

Example 1

Preparation of Human Undifferentiated Myeloid Cell Line KG-1cDNA Library (1) Preparation of Poly (A) RNA from KG-1 Cell KG-1 (ATCC CCL246), human undifferentiated myeloid cell line, was cultivated in the Iskov modified Dulbecco's medium (manufactured by Gibco BRL) to collect cells as pellet. To 1 ml of the cell pellet, 2.8 ml of a cytolytic solution [140 mM NaCl, 1.5 mM $MgCl_2$, 10 mM tris(hydroximethyl) aminomethane (Tris)-HCl (pH 8.5), 0.5% of Nonidet P-40] and 0.2 ml of 400 mM vanadyl sulfuric acid ribonucleotide complex were added. The cells were dissolved in the solution on the ice, superposed on 1 ml of a saccharose solution [140 mM NaCl, 1.5 mM $MgCl_2$, 10 mM Tris-HCl (pH 8.5), 1% Nonidet P-40, 24% saccharose], and centrifuged at 2° C. for 30 minutes at 30,000 rpm. To 4 ml of the supernatant containing RNA, 4 ml of an enzymatic reaction buffer [200 mM Tris-HCl (pH 7.5), 25 mM disodium ethylenediaminotetraacetate (EDTA), 300 mM NaCl, 2% lauryl sodium sulfate (SDS)] and 200 μl of 10 mg/ml proteinase K were added and allowed to react for 5 minutes at room temperature. To this reaction mixture, phenol extraction and chloroform extraction were carried out, and ethanol precipitation were carried out to recover RNA. After RNA was sufficiently dissolved in 4.5 ml of a buffer solution [20 mM Tris-HCl (pH 7.5), 0.1 mM EDTA, 0.1% SDS], it was heated at 70° C. for 5 minutes and chilled quickly, and then 0.5 ml of 5 M LiCl was added. The solution was centrifuged at 2° C. for 10 minutes at 8,000 rpm, the supernatant was heated at 70° C. for 5 minutes and chilled quickly, and then applied to an oligo d(T) cellulose column [Pasteur pipet charged with oligo dT cellulose (manufactured by Sigma)] which had been equilibrated with an absorption buffer [20 mM Tris-HCl (pH 7.5), 500 mM LiCl, 0.1 mM EDTA, 0.1% SDS]. The flow-through from the column was heated at 70° C. for 5 minutes and chilled quickly, and then applied to the column for absorbing poly (A) $^+$RNA again. The column was washed once with 1 ml of the absorption buffer, 3 times with 1.5 ml of the absorption buffer, 5 times with 1.5 ml of a washing buffer [20 mM Tris-HCl (pH 7.5) and 100 mM LiCl, 0.1 mM EDTA], and eluted with 3 ml of an elution buffer [10 mM Tris-HCl (pH 7.5), 0.1 mM EDTA] for recovering poly (A)$^+$RNA. From 6 ml (2 g) of the cell pellet, 8 mg of total RNA was obtained, and 200 μg of poly (A)$^+$RNA was obtained therefrom.

(2) Production of cDNA Library

A 8 μl (9.1 μg) portion of poly d(T)-NotI primer represented by SEQ ID NO:3, 32 μl of 5 mM Tris-HCl (pH 8.3) and 120 μl of distilled water were added to the obtained poly (A)$^+$RNA 40 μg (40 μl). DNA was synthesized by the method described in *Nucleic Acids Res.*, 12, 4539 (1984). It was heated at 70° C. for 10 minutes and chilled quickly, and then 62 μl of 5× reverse transcriptase reaction buffer [250 mM Tris-HCl (pH 8.3), 375 mM KCl, 15 mM $MgCl_2$], 32 μl of 100 ml dithiothreitol (DTT) and 8 μl of 20 mM dNTP (dATP, dGTP, dTTP, dCTP) were added thereto. After heating at 37° C. for 2 minutes, 3,200 units (16 μl) of reverse transcriptase SUPERSCRIPT RNase H$^-$ Reverse Transcriptase (manufactured by Gibco BRL) were added thereto, and the solution was allowed to react at 37° C. for 1 hour to synthesize cDNA. To the reaction mixture, 15 μl of 20 mM dNTP, 60 μl of 100 mM DTT, 16 μl of 15 mM β-nicotinamide dinucleotide and 929 μl of distilled water were added. Thereto further added was 32 units (16 μl) of *E. coli* ribonuclease H (manufactured by Takara Shuzo Co., Ltd.), 256 units (32 μl) of DNA polymerase I (manufactured by Takara Shuzo Co., Ltd.) and 480 units (8 μl) of *E. coli* DNA ligase (manufactured by Takara Shuzo Co., Ltd.), and allowed to react at 16° C. for 2 hours to prepare cDNA double-stranded. T4 DNA polymerase (48 units (24 μl)) was added and allowed to react at 16° C. for 5 minute to convert the termini blunt. EDTA (24 μl, 200 mM) was added thereto, and heated at 70° C. for 10 minutes to stop the reaction. The reaction mixture was subjected to phenol-chloroform extraction, and then ethanol precipitation was carried out. Additionally, ethanol precipitation was carried out two times to purify the cDNA. The double-stranded cDNA was dissolved in 40 μl of TE buffer [10 mM Tris-HCl (pH 8.0), 1 mM EDTA (pH 8.0)], and 60 μl of 10× restriction enzyme reaction buffer [500 mM Tris-HCl (pH 7.5), 100 mM $MgCl_2$, 10 mM DTT, 1M NaCl, 0.1% Triton X-100, 0.1% bovine serum albumin (BSA)] and 460 μl of distilled water were added thereto, and 320 units (40 μl) of restrictive enzyme NotI (manufactured by Takara Shuzo Co., Ltd.) were added thereto for digestion reaction at 37° C. for 2 hours. Moreover, 192 units (24 μl) of NotI were added thereto, and the reaction was carried out at 37° C. for 1 hour, and the reaction mixture was heated at 70° C. for 3 minutes to stop the reaction. After phenol/chloroform extraction, ethanol precipitation was carried out, and additionally, ehtanol precipitation was carried out two time to purify cDNA. The cDNA was centrifuged at 24,000 rpm for 24 hours with sucrose density gradient of 5 to 30% to separate into the fraction of larger than 6 kb, the fraction of 2 to 6 kb and the fraction of less than 2 kb. The fraction of 2 to 6 kb (0.5 μg) and 0.5 μg of plasmid vector pBluescript SK+ digested by NotI-EcoRV are ligated and introduced into *E. coli* DH10B (manufactured by Gibco) to prepare the cDNA library.

(3) Determination of Nucleotide Sequence of cDNA of Each Clone in KG-1cDNA Library The nucleotide sequence of cDNA of each clone in the library was determined using 373 DNA sequencer of Parkin Elmer. As specific reagents and method for the nucleotide sequence determination, Dye Primer Cycle Sequencing FS Ready Reaction Kit of Parkin Elmer were used in accordance with the manual attached to the kit. Thus obtained cDNA nucleotide sequences were collected to create a database.

Example 2

Cloning of cDNA Fragment of the Novel Gene KIAA0235

(1) Preparation of Total RNA from Leukocytes of IgA Nephropathy Patients and Healthy Persons A 20 ml portion of blood was collected from each of five IgA nephropathy patients and five healthy persons. Each blood sample was mixed with 500 μl of 1,000 units/ml heparin solution to inhibit coagulation, transferred into a centrifugation tube and then centrifuged at 3,300 rpm for 15 minutes at room temperature, and the resulting intermediate layer buffy coat containing leukocytes was transferred into another centrifugation tube. Thereafter, total RNAs were obtained in accordance with the AGPC method [Experimental Medicine, 9, 1937 (1991)].

(2) Fluorescence Differential Display Using Leukocyte Total RNAs of IgA Nephropathy Patients and Healthy Persons Distilled water was added to 2.5 μg of each of the total RNAs to a total volume of 9 μl, and the solution was mixed with 1 μl of an anchor primer (nucleotide sequence represented by SEQ ID NO:4, custom-synthesized by Sawady, 50 µM) whose 5'-end had been fluorescence-labeled with fluorescein isothiocyanate (referred to as "FITC" hereinafter), heated at 70° C. for 5 minutes and then immediately cooled on an ice bath. Thereto added were 2 µl of distilled water, 4 µl of 5× reverse transcriptase reaction buffer, 2 µl of 100 mM DTT, 1 µl of 10 mM dNTP and 1 µl (200 units) of reverse transcriptase SUPERSCRIPT RNase H⁻ Reverse Transcriptase (manufactured by Gibco BRL), the solution was mixed, allowed to react at 25° C. for 10 minutes and at 42° C. for 50 minutes to synthesize cDNA, and heated at 90° C. for 5 minutes to stop the reaction. To the reaction mixture, 80 µl of TE buffer was added.

To 1 µl of each synthesized cDNA, 14.7 µl of distilled water, 2 µl of 10×PCR buffer [100 mM Tris-HCl (pH 8.8), 500 mM KCl, 15 mM MgCl$_2$, 1% Triton X-100], 0.8 µl of 2.5 mM dNTP, 0.3 µl of 50 µM fluorescent labeling anchor primer FCH, 1 µl of arbitrary primer OPD-16 (nucleotide sequence represented by SEQ ID NO:5, manufactured by Operon, 10 µM) and 0.2 µl of DNA polymerase Gene Taq (manufactured by Nippon Gene Co., Ltd. 5 units/µl) were added and set to a thermal cycler. The PCR was effected by carrying out the reaction at 94° C. for 3 minutes, 40° C. for 5 minutes and 72° C. for 5 minutes, subsequently carrying out a total of 27 cycles of the reaction in which one cycle was composed of the steps of 95° C. for 15 seconds, 40° C. for 2 minutes and 72° C. for 1 minute, and finally carrying out 5 minutes of the reaction at 72° C.

A 3 µl portion of an electrophoresis sample solution (95% formaldehyde, 0.1% xylenecyanol, 0.1% bromphenol blue) to 4 µl of each PCR mixture, heated at 95° C. for 2 minutes and chilled immediately, and 6% acrylamide gel electrophoresis was conducted at and 1500 V for 2.5 hours. The electrophoresis buffer containing 89 mM Tris, 89 mM boric acid, 2 mM EDTA were used. Gel fluorescence after the electrophoresis was measured by a fluorimager (manufactured by Molecular Dynamics Inc.) for detecting and comparing the PCR amplified fragments. In comparison with 5 cases of the healthy persons, a band which significantly increased in leukocytes of 5 cases of the IgA nephropathy patients was recorded. Furthermore, total RNAs were prepared from other 3 cases of IgA nephropathy patients and 3 cases of healthy persons in the same manner to carry out the differential display in the same manner.

A band of about 200 bands which showed increased fluorescence in both of the above two trials of the differential display was cut off from the gel.

A 38 µl portion of distilled water, 5 µl of 10×PCR buffer, 4 µl of 2.5 mM dNTP, non-fluorescence labeling anchor primer NC (sequence listing represented by SEQ ID NO:4, produced by Sawady, 34 µm), 2 µl of 10 µM arbitrary primer OPD-16 (sequence listing represented by SEQ ID NO:5) and 0.5 µl of DNA polymerase Gene Taq were added to about ¼ portion of the gel thus cut off, the resulting mixture was heated at 94° C. for 3 minutes and then a total of 30 cycles of the reaction was carried out in which one cycle was comprised of the steps of 95° C. for 15 seconds, 40° C. for 2 minutes and 72° C. for 1 minute, subsequently carrying out 5 minutes of the reaction at 72° C. to complete PCR.

The resulting reaction solution was extracted with phenol-chloroform (1:1) and then with chloroformisoamyl alcohol (24:1), subsequently carrying out ethanol precipitation. The resulting precipitation was dissolved in 10 µl of TE buffer.

A 1 µl portion of amplified fragment and 1 µl of PCR fragment cloning vector pT7BlueT-Vector (manufactured by Novagen Inc.) were mixed and the amplified fragment was inserted into the plasmid using DNA ligation kit ver. 1 (manufactured by Takara Shuzo Co., Ltd.) according to the instructions of the kit. *E. coli* DH5α (manufactured by Gibco BRL) was transformed with the ligated mixture to obtain an ampicillin resistant transformant. Plasmid DNA was isolated for the transformant strain according to a publicly known method. A 0.3 ng portion of the plasmid DNA was dissolved into 19 µl of distilled water, and 2.5 µl of 10×PCR buffer, 2 µl of 2.5 mM dNTP, 0.3 µl of 34 µM anchor primer NC, 1 µl of 10 µM optional primer OPD-16 and 0.5 µl of DNA polymerase Gene Taq were added for performing PCR under the same conditions reamplification of amplified fragment. Since the fragment of about 200 bp was amplified, it was confirmed that the amplified fragment had been inserted into the plasmid.

(3) Determination of Amplified Fragment Nucleotide Sequence

The nucleotide sequence of the amplified fragment was determined by means of DNA sequencer (manufactured by Parkin Elmer). For the nucleotide sequence determination, reagents and method supplied by Dye Primer Cycle Sequencing FS Ready Reaction Kit of Parkin Elmer were used according to the instructions of the kit. The thus obtained nucleotide sequence corresponded to the DNA sequence 1076 to 1261 in SEQ ID NO:1. Thus obtained nucleotide sequence was compared with the nucleotide sequence database GenBank. The nucleotide sequence corresponding to the concerned nucleotide sequence was not identified among nucleotide sequences in the database, so that it was considered as cDNA fragment of a novel gene. Then the nucleotide sequence was compared with cDNA nucleotide sequence data base in the KG-1cDNA library, it was found to completely agree with a portion of cDNA nucleotide sequence of the gene KIAA0235, determining that KIAA0235 was a novel gene whose expression increases in the leukocyte of IgA nephropathy patients. As shown in SEQ ID NO:1, KIAA0235 was 5399 bp long and an open reading frame (ORF) composed of 850 amino acids exist therein. The amino acid sequence thereof is shown in SEQ ID NO:2. In the comparison of KIAA0235 nucleotide sequence with the database Genbank/EMBL, there are no identical nucleotide sequence, confirming that it concerns a novel gene cDNA. Moreover, when the amino acid sequence encoded by the cDNA ORF was compared with the database, it has shown a homology, at C terminal side, with the amino acid sequence of the pumilio gene [*Development*, 114, 221 (1992); *Cell*, 80, 747 (1995)] that is bound with mRNA of the hunchback gene derived from the mother, during the embryo development of Drosophila, and playing an important role in the formation of abdominal arthromere. It has also shown a homology of 82% with the amino acid sequence of the ORF of KIAA0099 [*DNA Research*, 2, 37 (1995)] already reported in the cDNA clone derived from this KG-1.

Example 3

Northern Blot of KIAA0235 in Human Cell and Various Tissues

Next, Northern blot was carried out to determine the expression of mRNA of the novel gene KIAA0235 in human cell and tissues.

Using filters manufactured by Clonetech blotting mRNA of human various tissues, the expression of mRNA of KIAA0235 in human various tissues was detected by means of Northern blot. Heart, brain, placenta, lung, lever, skeletal muscle, kidney and pancreas mRNAs were blotted on the filter, Human MTN blot. Spleen, thymus, prostate, testis, ovary, small intestine, colon and peripheral leukocyte mRNAs were blotted in the Human MTN Blot II. Concerning the cell, 2 μg of poly (A)+RNA obtained from human cervical carcinoma cell line, HeLa cell in the same manner as in Example 1 and poly (A) +RNA of KG-1 were applied to agarose gel electrophoresis, transferred to filter Biodyne A (manufactured by Paul Inc.), and KIAA0235 mRNA expression was detected by means of Northern blotting in the same manner. To use as probe, plasmid clone HA4677 containing KIAA0235 cDNA in the cDNA library prepared in Example 1 was cleaved by NotI (manufactured by Takara Shuzo Co., Ltd.) and HindIII (manufactured by Takara Shuzo Co., Ltd.) to purify KIAA0235 cDNA fragment. A 50 ng portion of this fragment were $^{32}$P labeled using [α-$^{32}$P] dCTP and BcaBEST labeling kit (manufactured by Takara Shuzo Co., Ltd.). Specific reagents and method of the labeling were complied with the instructions of the kit.

The filter was soaked in a hybridization solution (50% formaldehyde, 5×SSC, 5× Denhardt's solution (0.1% BSA, 0.1% ficoal, 0.1% polyvinyl pyrolidone, 0.25% SDS, 100 μg/ml of herring spermatozoa DNA which had been subjected to ultrasonic treatment and then denaturation (the process of seething in a microwave oven and chilled quickly in the ice was repeated 3 times), sealed and prehybridized overnight at 37° C. Next, the probe was denatured by seething in a microwave oven and chilling in the ice 3 times, added into the hybridization solution. The filter was soaked therein, sealed and hybridized overnight at 37° C.

The filter was taken out, washed by shaking in 1×SSC containing 0.1% SDS at room temperature. Changing the solution, it was washed furthermore several times, then rinsed with 0.1×SSC containing 0.5 SDS, and washed by shaking at 50° C. for 1 hour in 0.1×SSC containing 0.5% SDS. Finally, it was washed with 1×SSC containing 0.1% SDS and dried in the air. The filter was overlaid on the imaging plate (manufactured by Fuji Photo Film Co., Ltd.) for conducting the autoradiography for 4 hours, and analyzed with Bioimaging Analyzer BAS 2000 (manufactured by Fuji Photo Film Co. Ltd.). The results are shown in FIG. 1. Bands corresponding to mRNA of 2 different lengths, 5.5 kb and 6.8 kb, were detected in all tissues of heart, brain, placenta, lung, lever, skeletal muscle, kidney, pancreas, spleen, thymus, prostate, testis, ovary, small intestine, colon and peripheral leukocyte. Therefore, it was confirmed that KIAA0235 was a gene expressing ubiquitously in respective tissue. Moreover, bands corresponding to mRNA of 2 different lengths, 5.5 kb and 6.8 kb, were similarly detected in KG-1 and HeLa cells, and the expression of KIAA0235 in both cells was confirmed.

Example 4

Detection of Expression Specificity of KIAA0235 by RT-PCR

Using single-stranded cDNA synthesis kit, Superscript Preamplification System (manufactured by BRLs), to 2 μg of total RNA from leukocyte of 5 IgA nephropathy patients and 5 healthy persons obtained in Example 2, single-stranded cDNA was synthesized by oligo dT primer supplied by the kit. Specific reagents and method were complied with the protocol attached to the kit. After the reaction, 399 μl of distilled water was added to 21 μl of reaction mixture to be 420 μl as a whole, mRNA expression amount corresponding to each amplified fragment was measured by using 10 μl thereof according to RT-PCR. Namely, 15.8 μl of distilled water, 4 μl of 10×PCR buffer, 3.2 μl of 2.5 mM dNTP, 2 μl of DMSO, 2 μl of 10 μM KIAA0235 specific 5'-side sense primer (SEQ ID NO:6), 2 μl of 10 μM KIAA0235 specific 3'-side antisense primer (SEQ ID NO:7) and 2 μl of DNA polymerase GeneTag diluted to 1 unit/μl were added to 10 μl of leukocyte single-stranded cDNA, heated at 97° C. for 5 minutes, chilled quickly in the ice for 5 minutes. Subsequently, the PCR (a total of 30 cycles of the reaction in which one cycle was composed of the steps of 95° C. for 30 seconds, 65° C. for 1 minute and 72° C. for 2 minutes) was carried out.

Figure 2:
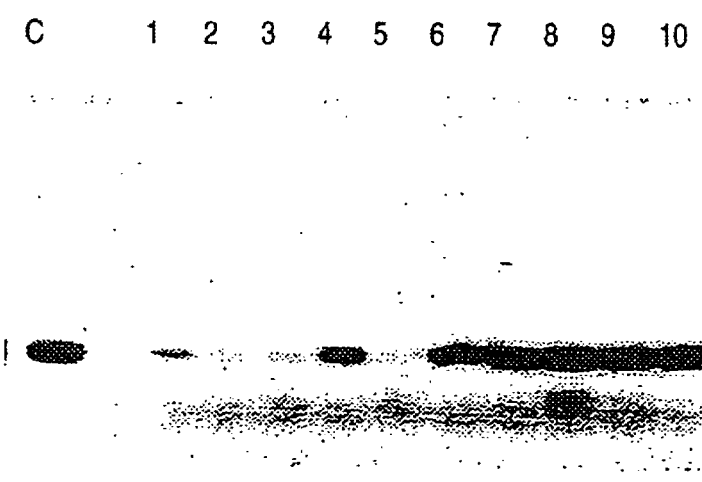
FIG. 2 shows the detection results of RT-PCR of KIAA0235 against the leukocyte of IgA nephropathy patients and healthy persons by the fluorimager in Example 4. 1 to 5 show the RT-PCR of the leukocyte of 5 healthy persons, 6 to 10 show that of 5 IgA nephropathy patients, and C shows PCR using as the template the plasmid to which the amplified fragment of the KIAA0235 cDNA obtained by differential display is introduced as the positive control.

In order to make a correction of the mRNA amount, with regard to glyceraldehyde-3-phosphate dehydrogenase (G3PDH) gene, a housekeeping gene, the similar reaction was carried out using a specific primer represented by SEQ ID NO:8 and NO:9, the mRNA expression amount of each gene was calibrated by the ratio of the expression amount of G3PDH mRNA, and then the average values of 5 IgA nephropathy patients and 5 healthy persons were compared. The results are shown in FIG. 2. It was confirmed that in the leukocyte of IgA nephropathy patients, KIAA0235 has expressed 6.6 times more than in healthy persons.

While the invention has been described in detail and with reference to specific embodiments thereof, it will be apparent to one skilled in the art that various changes and modifications can be made therein without departing from the spirit and scope thereof.

What is claimed is:

1. An isolated DNA, comprising the nucleotide sequence represented by SEQ ID NO:1.

2. A recombinant DNA which comprises a vector and the DNA according to claim 1.

3. A transformant obtained by introducing the recombinant DNA according to claim 2 into a host cell.

4. A diagnostic method for detecting an IgA nephropathy in a patient, comprising:

selecting an oligonucleotide comprising a 15 mer portion of the nucleotide sequence represented by SEQ ID NO:1;

selecting an oligonucleotide comprising a 15 mer portion of the nucleotide sequence complementary to the nucleotide sequence represented by SEQ ID NO:1;

using said oligonucleotides in a reverse-transcription-polymerase chain reaction to detect mRNA corresponding to the nucleotide sequence represented by SEQ ID NO:1; and determining an IgA nephropathy in said patient based on a result of said reverse-transcription-polymerase chain reaction.

5. A diagnostic method for detecting an IgA nephropathy in a patient, comprising:

selecting an oligonucleotide comprising a 15 mer portion of the nucleotide sequence complementary to the nucleotide sequence represented by SEQ ID NO:1;

using said olignucleotide in a Northern blot to detect mRNA corresponding to the nucleotide sequence represented by SEQ ID NO:1; and determining an IgA nephropathy in said patient based on a result of said Northern blot.

* * * * *

SEQUENCE LISTING

<160> NUMBER OF SEQ ID NOS: 9

<210> SEQ ID NO 1
<211> LENGTH: 5399
<212> TYPE: DNA
<213> ORGANISM: Homo sapiens
<220> FEATURE:
<221> NAME/KEY: CDS
<222> LOCATION: (2)..(2551)
<223> OTHER INFORMATION: Cell Line KG-1

<400> SEQUENCE: 1

```
a gaa ttt tca aat cct gaa act cag aat ctg gat gcc atg gaa caa gtt      49
  Glu Phe Ser Asn Pro Glu Thr Gln Asn Leu Asp Ala Met Glu Gln Val
  1               5                  10                  15
```

-continued

```
ggt ctg gaa tcc tta cag ttt gac tat cct ggt aat cag gta cca atg        97
Gly Leu Glu Ser Leu Gln Phe Asp Tyr Pro Gly Asn Gln Val Pro Met
         20                  25                  30 gac tct tca gga gct act gta ggc ctt ttt gac tac aat tcc cag cag       145
Asp Ser Ser Gly Ala Thr Val Gly Leu Phe Asp Tyr Asn Ser Gln Gln
             35                  40                  45 cag ctc ttt cag agg act aat gca cta aca gtt caa cag tta act gca       193
Gln Leu Phe Gln Arg Thr Asn Ala Leu Thr Val Gln Gln Leu Thr Ala
     50                  55                  60 gct caa cag cag caa tat gca tta gca gca gct cag cag cca cat ata       241
Ala Gln Gln Gln Gln Tyr Ala Leu Ala Ala Ala Gln Gln Pro His Ile
 65                  70                  75                  80 gct ggt gta ttc tca gca ggc ctt gct cca gct gca ttt gtg cca aat       289
Ala Gly Val Phe Ser Ala Gly Leu Ala Pro Ala Ala Phe Val Pro Asn
                 85                  90                  95 cca tac att att agt gct gct cct cca ggg acc gat ccg tat act gca       337
Pro Tyr Ile Ile Ser Ala Ala Pro Pro Gly Thr Asp Pro Tyr Thr Ala
             100                 105                 110 gca gga ttg gct gca gca gct aca tta gca ggt cca gca gtg gtt cca       385
Ala Gly Leu Ala Ala Ala Ala Thr Leu Ala Gly Pro Ala Val Val Pro
     115                 120                 125 cct cag tat tac ggc gtt cca tgg ggg gtg tat cca gcc aac tta ttt       433
Pro Gln Tyr Tyr Gly Val Pro Trp Gly Val Tyr Pro Ala Asn Leu Phe
 130                 135                 140 cag cag caa gct gca gct gcg gca aat aac aca gcc agt cag caa gca       481
Gln Gln Gln Ala Ala Ala Ala Ala Asn Asn Thr Ala Ser Gln Gln Ala
145                 150                 155                 160 gca tca caa gct cag cct gga cag caa cag gtt ctc cgt gct gga gca       529
Ala Ser Gln Ala Gln Pro Gly Gln Gln Gln Val Leu Arg Ala Gly Ala
                 165                 170                 175 ggt cag cgt cct ctt act ccc aat cag ggt cag caa ggg cag caa gca       577
Gly Gln Arg Pro Leu Thr Pro Asn Gln Gly Gln Gln Gly Gln Gln Ala
             180                 185                 190 gaa tca ctt gcg gca gct gca gca gca aat cca aca ttg gct ttt ggt       625
Glu Ser Leu Ala Ala Ala Ala Ala Ala Asn Pro Thr Leu Ala Phe Gly
     195                 200                 205 cag ggt ctt gct act ggc atg cca ggc tat caa gta cta gct cca act       673
Gln Gly Leu Ala Thr Gly Met Pro Gly Tyr Gln Val Leu Ala Pro Thr
 210                 215                 220 gcc tat tat gat cag act ggt gcc tta gtg gtt ggc cct gga gca agg       721
Ala Tyr Tyr Asp Gln Thr Gly Ala Leu Val Val Gly Pro Gly Ala Arg
225                 230                 235                 240 act ggc ctt gga gct cca gtt cgg tta atg gct cca aca cct gtt tta       769
Thr Gly Leu Gly Ala Pro Val Arg Leu Met Ala Pro Thr Pro Val Leu
                 245                 250                 255 att agt tca gca gca gca caa gct gca gca gca gca gct gga gga           817
Ile Ser Ser Ala Ala Ala Gln Ala Ala Ala Ala Ala Ala Gly Gly
             260                 265                 270 act gca agt agc ctt aca ggc agc aca aat ggt ctg ttt cgg cca att       865
Thr Ala Ser Ser Leu Thr Gly Ser Thr Asn Gly Leu Phe Arg Pro Ile
     275                 280                 285 ggc act cag cca cca cag cag cag caa cag cag cca agc act aat ctg       913
Gly Thr Gln Pro Pro Gln Gln Gln Gln Gln Pro Ser Thr Asn Leu
 290                 295                 300 caa tct aat tca ttt tat gga agc agt tct ttg act aat agc tcc cag       961
Gln Ser Asn Ser Phe Tyr Gly Ser Ser Ser Leu Thr Asn Ser Ser Gln
305                 310                 315                 320 agt agt tct tta ttt tct cat gga cct ggt caa cct gga agt aca tct      1009
Ser Ser Ser Leu Phe Ser His Gly Pro Gly Gln Pro Gly Ser Thr Ser
```

-continued

|  |  |  |  |  |  |  |  |  |  |  |  |  |  |  |  |  |
|---|---|---|---|---|---|---|---|---|---|---|---|---|---|---|---|---|
|  | 325 |  |  |  |  | 330 |  |  |  |  | 335 |  |  |  |  |  |
| ctt | ggc | ttt | gga | agt | ggt | aac | tct | ttg | ggt | gct | gct | ata | ggc | tca | gcc | 1057 |
| Leu | Gly | Phe | Gly | Ser | Gly | Asn | Ser | Leu | Gly | Ala | Ala | Ile | Gly | Ser | Ala |  |
|  |  |  | 340 |  |  |  |  | 345 |  |  |  |  | 350 |  |  |  |
| ctc | agt | gga | ttt | ggt | tca | tca | gtt | ggc | agt | tct | gca | agt | agt | agt | gcc | 1105 |
| Leu | Ser | Gly | Phe | Gly | Ser | Ser | Val | Gly | Ser | Ser | Ala | Ser | Ser | Ser | Ala |  |
|  |  | 355 |  |  |  |  | 360 |  |  |  |  | 365 |  |  |  |  |
| aca | agg | aga | gag | tct | cta | tct | act | agc | tct | gac | ttg | tac | aaa | aga | tct | 1153 |
| Thr | Arg | Arg | Glu | Ser | Leu | Ser | Thr | Ser | Ser | Asp | Leu | Tyr | Lys | Arg | Ser |  |
|  | 370 |  |  |  |  | 375 |  |  |  |  | 380 |  |  |  |  |  |
| agt | agc | agc | cta | gca | ccc | ata | ggg | caa | cca | ttt | tac | aat | agt | ctg | gga | 1201 |
| Ser | Ser | Ser | Leu | Ala | Pro | Ile | Gly | Gln | Pro | Phe | Tyr | Asn | Ser | Leu | Gly |  |
| 385 |  |  |  |  | 390 |  |  |  |  | 395 |  |  |  |  | 400 |  |
| ttt | tcc | tcc | tct | cca | agt | cca | ata | ggc | atg | cct | ctg | cca | agc | caa | act | 1249 |
| Phe | Ser | Ser | Ser | Pro | Ser | Pro | Ile | Gly | Met | Pro | Leu | Pro | Ser | Gln | Thr |  |
|  |  |  |  | 405 |  |  |  |  | 410 |  |  |  |  | 415 |  |  |
| cca | gga | cat | tca | ctt | acg | cca | ccg | cca | tca | ctt | tca | tca | cat | gga | tcc | 1297 |
| Pro | Gly | His | Ser | Leu | Thr | Pro | Pro | Pro | Ser | Leu | Ser | Ser | His | Gly | Ser |  |
|  |  |  | 420 |  |  |  |  | 425 |  |  |  |  | 430 |  |  |  |
| tca | tcc | agt | ttg | cat | tta | gga | gga | ctg | aca | aat | ggt | agt | ggt | cga | tat | 1345 |
| Ser | Ser | Ser | Leu | His | Leu | Gly | Gly | Leu | Thr | Asn | Gly | Ser | Gly | Arg | Tyr |  |
|  |  | 435 |  |  |  |  | 440 |  |  |  |  | 445 |  |  |  |  |
| atc | tct | gca | gca | cct | gga | gca | gaa | gca | aaa | tat | cga | agt | gct | tca | agc | 1393 |
| Ile | Ser | Ala | Ala | Pro | Gly | Ala | Glu | Ala | Lys | Tyr | Arg | Ser | Ala | Ser | Ser |  |
| 450 |  |  |  |  | 455 |  |  |  |  | 460 |  |  |  |  |  |  |
| act | tcc | agt | cta | ttt | agc | tcc | agc | agc | cag | ctc | ttt | cct | cct | tcc | cgg | 1441 |
| Thr | Ser | Ser | Leu | Phe | Ser | Ser | Ser | Gln | Leu | Phe | Pro | Pro | Ser | Arg |  |  |
| 465 |  |  |  |  | 470 |  |  |  |  | 475 |  |  |  |  | 480 |  |
| ctt | cgg | tat | aat | agg | tct | gat | att | atg | cct | tct | ggc | cgc | agt | aga | tta | 1489 |
| Leu | Arg | Tyr | Asn | Arg | Ser | Asp | Ile | Met | Pro | Ser | Gly | Arg | Ser | Arg | Leu |  |
|  |  |  |  | 485 |  |  |  |  | 490 |  |  |  |  | 495 |  |  |
| ttg | gaa | gat | ttc | aga | aac | aac | cgc | ttc | cca | aac | ctt | cag | ctt | aga | gac | 1537 |
| Leu | Glu | Asp | Phe | Arg | Asn | Asn | Arg | Phe | Pro | Asn | Leu | Gln | Leu | Arg | Asp |  |
|  |  |  | 500 |  |  |  |  | 505 |  |  |  |  | 510 |  |  |  |
| ttg | att | gga | cat | ata | gtt | gag | ttt | tct | caa | gac | cag | cat | ggt | tct | aga | 1585 |
| Leu | Ile | Gly | His | Ile | Val | Glu | Phe | Ser | Gln | Asp | Gln | His | Gly | Ser | Arg |  |
|  |  | 515 |  |  |  |  | 520 |  |  |  |  | 525 |  |  |  |  |
| ttc | ata | cag | caa | aaa | cta | gag | aga | gct | act | cca | gct | gag | cga | cag | atg | 1633 |
| Phe | Ile | Gln | Gln | Lys | Leu | Glu | Arg | Ala | Thr | Pro | Ala | Glu | Arg | Gln | Met |  |
|  | 530 |  |  |  |  | 535 |  |  |  |  | 540 |  |  |  |  |  |
| gta | ttt | aat | gaa | att | ctg | caa | gca | gcc | tat | caa | tta | atg | act | gat | gtt | 1681 |
| Val | Phe | Asn | Glu | Ile | Leu | Gln | Ala | Ala | Tyr | Gln | Leu | Met | Thr | Asp | Val |  |
| 545 |  |  |  |  | 550 |  |  |  |  | 555 |  |  |  |  | 560 |  |
| ttt | ggc | aac | tat | gtt | ata | cag | aag | ttt | ttt | gag | ttt | ggg | agt | ctg | gat | 1729 |
| Phe | Gly | Asn | Tyr | Val | Ile | Gln | Lys | Phe | Phe | Glu | Phe | Gly | Ser | Leu | Asp |  |
|  |  |  |  | 565 |  |  |  |  | 570 |  |  |  |  | 575 |  |  |
| caa | aaa | tta | gcc | ctg | gct | act | cgt | att | cgt | ggt | cat | gtt | cta | ccc | tta | 1777 |
| Gln | Lys | Leu | Ala | Leu | Ala | Thr | Arg | Ile | Arg | Gly | His | Val | Leu | Pro | Leu |  |
|  |  |  | 580 |  |  |  |  | 585 |  |  |  |  | 590 |  |  |  |
| gcc | ttg | cag | atg | tat | ggc | tgc | cgc | gtt | att | cag | aaa | gca | tta | gaa | tct | 1825 |
| Ala | Leu | Gln | Met | Tyr | Gly | Cys | Arg | Val | Ile | Gln | Lys | Ala | Leu | Glu | Ser |  |
|  |  | 595 |  |  |  |  | 600 |  |  |  |  | 605 |  |  |  |  |
| att | tct | tct | gac | cag | cag | agt | gaa | atg | gta | aag | gag | ctg | gat | ggt | cat | 1873 |
| Ile | Ser | Ser | Asp | Gln | Gln | Ser | Glu | Met | Val | Lys | Glu | Leu | Asp | Gly | His |  |
|  | 610 |  |  |  |  | 615 |  |  |  |  | 620 |  |  |  |  |  |
| gtg | ctc | aaa | tgt | gtg | aaa | gat | cag | aat | gga | aac | cat | gtt | gta | caa | aaa | 1921 |
| Val | Leu | Lys | Cys | Val | Lys | Asp | Gln | Asn | Gly | Asn | His | Val | Val | Gln | Lys |  |
| 625 |  |  |  |  | 630 |  |  |  |  | 635 |  |  |  |  | 640 |  |
| tgt | atc | gaa | tgt | gtt | cag | cca | cag | tca | cta | cag | ttc | atc | att | gat | gct | 1969 |

-continued

| | |
|---|---|
| Cys Ile Glu Cys Val Gln Pro Gln Ser Leu Gln Phe Ile Ile Asp Ala<br>              645                    650              655 | |
| ttc aag gga caa gta ttt gtg ctt tca act cat cct tat ggc tgc aga<br>Phe Lys Gly Gln Val Phe Val Leu Ser Thr His Pro Tyr Gly Cys Arg<br>             660                    665              670 | 2017 |
| gta att cag cgc atc cta gag cat tgc act gca gaa cag acc tta cct<br>Val Ile Gln Arg Ile Leu Glu His Cys Thr Ala Glu Gln Thr Leu Pro<br>       675                   680              685 | 2065 |
| atc tta gaa gaa ctc cac caa cat aca gag cag ttg gta cag gat cag<br>Ile Leu Glu Glu Leu His Gln His Thr Glu Gln Leu Val Gln Asp Gln<br>     690                    695              700 | 2113 |
| tat ggc aat tat gtt att cag cat gta ctg gaa cac ggt cga cct gaa<br>Tyr Gly Asn Tyr Val Ile Gln His Val Leu Glu His Gly Arg Pro Glu<br>705                  710              715              720 | 2161 |
| gac aag agc aaa att gtt tcc gaa atc agg gga aag gtt tta gcc ctg<br>Asp Lys Ser Lys Ile Val Ser Glu Ile Arg Gly Lys Val Leu Ala Leu<br>             725                730              735 | 2209 |
| agt caa cac aaa ttt gcc agc aat gta gta gaa aag tgt gtt act cat<br>Ser Gln His Lys Phe Ala Ser Asn Val Val Glu Lys Cys Val Thr His<br>             740                745              750 | 2257 |
| gcc tcc cgt gct gag aga gct tta ctg att gac gag gtt tgc tgc cag<br>Ala Ser Arg Ala Glu Arg Ala Leu Leu Ile Asp Glu Val Cys Cys Gln<br>       755                  760              765 | 2305 |
| aat gat ggt cct cac agt gcc tta tac acc atg atg aag gac cag tat<br>Asn Asp Gly Pro His Ser Ala Leu Tyr Thr Met Met Lys Asp Gln Tyr<br>770                  775              780 | 2353 |
| gcc aat tac gtg gtt caa aag atg att gat atg gct gaa cct gct cag<br>Ala Asn Tyr Val Val Gln Lys Met Ile Asp Met Ala Glu Pro Ala Gln<br>785                  790              795              800 | 2401 |
| aga aag ata atc atg cac aag att cga cct cac att act act ttg cgc<br>Arg Lys Ile Ile Met His Lys Ile Arg Pro His Ile Thr Thr Leu Arg<br>             805                810              815 | 2449 |
| aaa tac aca tac ggg aag cat ata ctg gcc aag ttg gaa aag tat tat<br>Lys Tyr Thr Tyr Gly Lys His Ile Leu Ala Lys Leu Glu Lys Tyr Tyr<br>             820                825              830 | 2497 |
| ttg aag aat agc ccg gac cta gga cct att gga gga cca cca aat gga<br>Leu Lys Asn Ser Pro Asp Leu Gly Pro Ile Gly Gly Pro Pro Asn Gly<br>              835              840              845 | 2545 |
| atg ctg taaattacag gagcaagaga aagaagataa tttaaccatg tgaaaagaat<br>Met Leu<br>     850 | 2601 |
| tttttttgtgc gtgaattatc aaaacacaac tcaactatga atcttcaatt tttttttaaa | 2661 |
| gcaaaactat ttattgactt tattcatcca tttgtaaatt ttttaaggtt cttgtgtata | 2721 |
| tttgggggggt gggggatgaa ttataaatta tattcagccc tgagtggaga cctatcagat | 2781 |
| tggattgctg gcaaagcaca gaatgcctgt atatgatgta actgtatcaa aaataaaaag | 2841 |
| ctgtcacata ttttgtaaat ttttaccttg taaagtcaca aaaatagttt ttaaaggaaa | 2901 |
| aagtacagta ttctttttaat aaactggctc acagtctggt aggtctacaa ccccatagca | 2961 |
| caacaggttt atagagatgt atatagaatt atagtcctta ttttttttcct ttgcgtgaaa | 3021 |
| ccttttataa cagattaaca atcaactgca taaatattat taatattta aaagagtta | 3081 |
| agttgtatttt tgataattca caaactatca tgcaaataac gagtaagtag acaagaataa | 3141 |
| agtggtttga gatgaaaaga acctaacatt atttacagta gatgtggttt taatacaatt | 3201 |
| actgccctaa aatgtctctg gcaatgtaca gaaatattgt atatacttac atatgtaatt | 3261 |
| gttgtaagag ttaaatacaa aatcatggtg acacttccaa ttaagtgcac taaatgaaaa | 3321 |

```
gttaagtcac ttattaactt ttcagttttgg tttgcaatga gaaagagtgg aaatttgtat      3381
tttgttttgc ttatagaatt acagacatgt tgaggaagtg ttgagcttta ttttgctttt      3441
tcatagaggc agaaagtagg aaccagatag agatgaaaag gggccactga aaagtgaatt      3501
tgatagctca gcatttaagc atgattacat attcagatag ctcttttgc tttctataaa       3561 tatatgcatt gtgtgtgtag taatagatgt aagtttacac tttgaaagga aatcttgttt      3621
caatgtttat tataaaagcc ttgctaattt agtagtgatg cttttccttgg ttgtacaggt     3681 gtacatttgt aaaccttcat gctgtaaatg gaatttgttt tatctctttg ggatacattt      3741
gcattttagt gtacatttac gtccctgccc tctttgacct ggcaatatag tgttgtataa      3801
tgtaaattta tttctccaaa tcgagagtga ttttttaaaa attttttatc tttatatggt      3861
ttcagaagta tgaaccagct ttcttttttat tattgtgaga tcattttgtt ttataacata    3921
gttgttgact gttaatatgg acctgctaga atttggatca ctttcaattg aagtcagggt      3981
attgtgcata atagaaagta ttggactgag atatttggtt accatggagg ccaatgcttt     4041
tttcatctta ttaaatgtga tgtgactttt tctttgtac agaagagtac tgtattttg       4101 aatagcctac tcccaagtaa gagcaaatct gtatgataac atttttttcct ctggacataa    4161 gacataacag taacacgatg tacatttaca agcggcctta tgtacatttc ccaacaatct     4221
ttttaaggca aaattgtgac catatgtgta taattaaaat cgttttaat cctttgccta      4281 tgaaatatt ttggaaaaaa acttgctgtg tatattcagt ttctgaaaga taaagaaagt      4341
gctttgtatt ttgttgaagt cagtatttttg tataaacatt tatgttgacc cacttatgtt    4401
cagtgctgaa aactaaaatg aacatgctat tctgtcagct gaatatggaa gagatctttt     4461
tttactagag atctgcagaa gaaacgcaat cttctgagca caatatggaa tctaaaggtt     4521
ttatcactta gttgttcata ttatgaacct aaaaataatg gcataaagtt tggggatgcc     4581
aggcatactt tttcatgttt ggtgttgagt tattttactt ttctaaccca acattccttg     4641
gtgagaccat taaatccaaa cacttgtcac cgttccttct catagtcact ctgggtcatc    4701
agcatgtccc agtcactgca gcaacgcctt gtgtttgttt catttttta aaacccacac     4761 aaagccgctg tctcactttt tcctacttta ccaacctcag agtatttcgg cccgtatcga    4821
acttttgttc tcagtatcag cccatggttt caggatcaaa gctgtcatgt tggagattgg    4881
taatggcttt cctgtctttg tacagttgaa ttcctagtct tccttcatcc ttgccctctg    4941
ttggcacagg cattatctct gcaattttag aaaatgacaa gtagagaata ctacattgag     5001
aaactaaacc ctcttcttgg ggtcctgata ctcattccca tttgtcccag tgctgacaac     5061
ccaatcttcc caatactttc aggcctgctc tacaaaagta cctgttcttg tagaaatttt    5121
acagtctgcc attttgggtg cccaccccaa tttttacctt ttagtaagtt ggcatgaaat    5181
tttggtaaaa tctgaaaatc acatttcaga ataaacaat tgggcaaaac tacctaggct      5241
ttactcttga gtgtctcctt tgataggga ttgtttctgg accagtttgt ctaagtcctg      5301
gctcttattg gttcatatga aataatgtta acttcacttc tttgtatatt atgtataaat     5361
tagaaaatga aaaatgtgtg aataacattg tatgaaat                             5399
```

<210> SEQ ID NO 2
<211> LENGTH: 850
<212> TYPE: PRT
<213> ORGANISM: Homo sapiens

<400> SEQUENCE: 2

Glu Phe Ser Asn Pro Glu Thr Gln Asn Leu Asp Ala Met Glu Gln Val

```
              1               5                  10                 15
        Gly Leu Glu Ser Leu Gln Phe Asp Tyr Pro Gly Asn Gln Val Pro Met
                        20                  25                  30
        Asp Ser Ser Gly Ala Thr Val Gly Leu Phe Asp Tyr Asn Ser Gln Gln
                        35                  40                  45
        Gln Leu Phe Gln Arg Thr Asn Ala Leu Thr Val Gln Gln Leu Thr Ala
                    50                  55                  60
        Ala Gln Gln Gln Gln Tyr Ala Leu Ala Ala Gln Gln Pro His Ile
        65                  70                  75                  80
        Ala Gly Val Phe Ser Ala Gly Leu Ala Pro Ala Phe Val Pro Asn
                        85                  90                  95
        Pro Tyr Ile Ile Ser Ala Ala Pro Gly Thr Asp Pro Tyr Thr Ala
                        100                 105                 110
        Ala Gly Leu Ala Ala Ala Ala Thr Leu Ala Gly Pro Ala Val Val Pro
                        115                 120                 125
        Pro Gln Tyr Tyr Gly Val Pro Trp Gly Val Tyr Pro Ala Asn Leu Phe
                        130                 135                 140
        Gln Gln Gln Ala Ala Ala Ala Asn Asn Thr Ala Ser Gln Gln Ala
        145                 150                 155                 160
        Ala Ser Gln Ala Gln Pro Gly Gln Gln Val Leu Arg Ala Gly Ala
                        165                 170                 175
        Gly Gln Arg Pro Leu Thr Pro Asn Gln Gly Gln Gly Gln Gln Ala
                        180                 185                 190
        Glu Ser Leu Ala Ala Ala Ala Ala Asn Pro Thr Leu Ala Phe Gly
                        195                 200                 205
        Gln Gly Leu Ala Thr Gly Met Pro Gly Tyr Gln Val Leu Ala Pro Thr
                        210                 215                 220
        Ala Tyr Tyr Asp Gln Thr Gly Ala Leu Val Val Gly Pro Gly Ala Arg
        225                 230                 235                 240
        Thr Gly Leu Gly Ala Pro Val Arg Leu Met Ala Pro Thr Pro Val Leu
                        245                 250                 255
        Ile Ser Ser Ala Ala Ala Gln Ala Ala Ala Ala Ala Ala Gly Gly
                        260                 265                 270
        Thr Ala Ser Ser Leu Thr Gly Ser Thr Asn Gly Leu Phe Arg Pro Ile
                        275                 280                 285
        Gly Thr Gln Pro Pro Gln Gln Gln Gln Gln Pro Ser Thr Asn Leu
                        290                 295                 300
        Gln Ser Asn Ser Phe Tyr Gly Ser Ser Leu Thr Asn Ser Ser Gln
        305                 310                 315                 320
        Ser Ser Ser Leu Phe Ser His Gly Pro Gly Gln Pro Gly Ser Thr Ser
                        325                 330                 335
        Leu Gly Phe Gly Ser Gly Asn Ser Leu Gly Ala Ala Ile Gly Ser Ala
                        340                 345                 350
        Leu Ser Gly Phe Gly Ser Ser Val Gly Ser Ser Ala Ser Ser Ser Ala
                        355                 360                 365
        Thr Arg Arg Glu Ser Leu Ser Thr Ser Ser Asp Leu Tyr Lys Arg Ser
                        370                 375                 380
        Ser Ser Ser Leu Ala Pro Ile Gly Gln Pro Phe Tyr Asn Ser Leu Gly
        385                 390                 395                 400
        Phe Ser Ser Ser Pro Ser Ile Gly Met Pro Leu Pro Ser Gln Thr
                        405                 410                 415
        Pro Gly His Ser Leu Thr Pro Pro Ser Leu Ser Ser His Gly Ser
                        420                 425                 430
```

```
Ser Ser Ser Leu His Leu Gly Gly Leu Thr Asn Gly Ser Gly Arg Tyr
        435                 440                 445

Ile Ser Ala Ala Pro Gly Ala Glu Ala Lys Tyr Arg Ser Ala Ser Ser
        450                 455                 460

Thr Ser Ser Leu Phe Ser Ser Ser Gln Leu Phe Pro Pro Ser Arg
465                 470                 475                 480

Leu Arg Tyr Asn Arg Ser Asp Ile Met Pro Ser Gly Arg Ser Arg Leu
                485                 490                 495

Leu Glu Asp Phe Arg Asn Asn Arg Phe Pro Asn Leu Gln Leu Arg Asp
                500                 505                 510

Leu Ile Gly His Ile Val Glu Phe Ser Gln Asp Gln His Gly Ser Arg
                515                 520                 525

Phe Ile Gln Gln Lys Leu Glu Arg Ala Thr Pro Ala Glu Arg Gln Met
                530                 535                 540

Val Phe Asn Glu Ile Leu Gln Ala Ala Tyr Gln Leu Met Thr Asp Val
545                 550                 555                 560

Phe Gly Asn Tyr Val Ile Gln Lys Phe Phe Glu Phe Gly Ser Leu Asp
                565                 570                 575

Gln Lys Leu Ala Leu Ala Thr Arg Ile Arg Gly His Val Leu Pro Leu
                580                 585                 590

Ala Leu Gln Met Tyr Gly Cys Arg Val Ile Gln Lys Ala Leu Glu Ser
                595                 600                 605

Ile Ser Ser Asp Gln Gln Ser Glu Met Val Lys Glu Leu Asp Gly His
                610                 615                 620

Val Leu Lys Cys Val Lys Asp Gln Asn Gly Asn His Val Val Gln Lys
625                 630                 635                 640

Cys Ile Glu Cys Val Gln Pro Gln Ser Leu Gln Phe Ile Ile Asp Ala
                645                 650                 655

Phe Lys Gly Gln Val Phe Val Leu Ser Thr His Pro Tyr Gly Cys Arg
                660                 665                 670

Val Ile Gln Arg Ile Leu Glu His Cys Thr Ala Glu Gln Thr Leu Pro
                675                 680                 685

Ile Leu Glu Glu Leu His Gln His Thr Glu Gln Leu Val Gln Asp Gln
                690                 695                 700

Tyr Gly Asn Tyr Val Ile Gln His Val Leu Glu His Gly Arg Pro Glu
705                 710                 715                 720

Asp Lys Ser Lys Ile Val Ser Glu Ile Arg Gly Lys Val Leu Ala Leu
                725                 730                 735

Ser Gln His Lys Phe Ala Ser Asn Val Val Glu Lys Cys Val Thr His
                740                 745                 750

Ala Ser Arg Ala Glu Arg Ala Leu Leu Ile Asp Glu Val Cys Cys Gln
                755                 760                 765

Asn Asp Gly Pro His Ser Ala Leu Tyr Thr Met Met Lys Asp Gln Tyr
                770                 775                 780

Ala Asn Tyr Val Val Gln Lys Met Ile Asp Met Ala Glu Pro Ala Gln
785                 790                 795                 800

Arg Lys Ile Ile Met His Lys Ile Arg Pro His Ile Thr Thr Leu Arg
                805                 810                 815

Lys Tyr Thr Tyr Gly Lys His Ile Leu Ala Lys Leu Glu Lys Tyr Tyr
                820                 825                 830

Leu Lys Asn Ser Pro Asp Leu Gly Pro Ile Gly Gly Pro Pro Asn Gly
                835                 840                 845
```

Met Leu
    850

<210> SEQ ID NO 3
<211> LENGTH: 50
<212> TYPE: DNA
<213> ORGANISM: Artificial Sequence
<220> FEATURE:
<223> OTHER INFORMATION: other nucleic acid from homo sapiens,
      synthesized DNA

<400> SEQUENCE: 3
ctctagaggc ggccgctttt tttttttttt tttttttttt tttttttttt           50

<210> SEQ ID NO 4
<211> LENGTH: 17
<212> TYPE: DNA
<213> ORGANISM: Artificial Sequence
<220> FEATURE:
<223> OTHER INFORMATION: other nucleic acid from homo sapiens,
      synthesized DNA

<400> SEQUENCE: 4 gtttttttttt tttttttc                                             17

<210> SEQ ID NO 5
<211> LENGTH: 10
<212> TYPE: DNA
<213> ORGANISM: Artificial Sequence
<220> FEATURE:
<223> OTHER INFORMATION: other nucleic acid from homo sapiens,
      synthesized DNA

<400> SEQUENCE: 5
agggcgtaag                                                       10

<210> SEQ ID NO 6
<211> LENGTH: 22
<212> TYPE: DNA
<213> ORGANISM: Artificial Sequence
<220> FEATURE:
<223> OTHER INFORMATION: other nucleic acid from homo sapiens,
      synthesized DNA

<400> SEQUENCE: 6
gcatgcctat tggacttggg ga                                         22

<210> SEQ ID NO 7
<211> LENGTH: 24
<212> TYPE: DNA
<213> ORGANISM: Artificial Sequence
<220> FEATURE:
<223> OTHER INFORMATION: other nucleic acid from homo sapiens,
      synthesized DNA

<400> SEQUENCE: 7
gttggcagtt ctgcaagtag tagt                                       24

<210> SEQ ID NO 8
<211> LENGTH: 22
<212> TYPE: DNA
<213> ORGANISM: Artificial Sequence
<220> FEATURE:
<223> OTHER INFORMATION: other nucelic acid from homo sapiens,
      synthesized DNA

<400> SEQUENCE: 8

```
cccatcacca tcttccagga gc                                                  22
```

<210> SEQ ID NO 9
<211> LENGTH: 26
<212> TYPE: DNA
<213> ORGANISM: Artificial Sequence
<220> FEATURE:
<223> OTHER INFORMATION: other nucleic acid from homo sapiens,
      synthesized DNA

<400> SEQUENCE: 9

```
ttcaccacct tcttgatgtc atcata                                              26
```